(12) United States Patent
Lu et al.

(10) Patent No.: US 8,298,199 B2
(45) Date of Patent: Oct. 30, 2012

(54) PRESSURE BANDAGE

(75) Inventors: Wei-Hua Lu, Pingtung (TW);
Yung-Chuan Chen, Pingtung (TW);
Ting-Lung Chiang, Pingtung (TW)

(73) Assignee: National Pingtun University of Science and Technology, Pingtung (TW)

( * ) Notice: Subject to any disclaimer, the term of this patent is extended or adjusted under 35 U.S.C. 154(b) by 330 days.

(21) Appl. No.: 12/768,797

(22) Filed: Apr. 28, 2010

(65) Prior Publication Data
US 2011/0040265 A1 Feb. 17, 2011

(30) Foreign Application Priority Data
Aug. 11, 2009 (TW) ................................ 98126914 A

(51) Int. Cl.
*A61F 13/00* (2006.01)
*A61M 35/00* (2006.01)
(52) U.S. Cl. ......................................... 604/304; 602/53
(58) Field of Classification Search ...................... 602/53
See application file for complete search history.

(56) References Cited

U.S. PATENT DOCUMENTS

| 3,687,143 | A | | 8/1972 | Schneeberger et al. |
| 4,005,709 | A | | 2/1977 | Laerdal |
| 4,817,595 | A | | 4/1989 | Maass |
| 5,267,952 | A | | 12/1993 | Gardner |
| 5,643,315 | A | * | 7/1997 | Daneshvar ..................... 606/201 |
| 2005/0106225 | A1 | * | 5/2005 | Massengale et al. .......... 424/448 |
| 2008/0132820 | A1 | * | 6/2008 | Buckman et al. ............... 602/48 |
| 2009/0182255 | A1 | * | 7/2009 | Hay et al. ......................... 602/53 |

* cited by examiner

*Primary Examiner* — Melanie Hand
*Assistant Examiner* — Andrew S Lo
(74) *Attorney, Agent, or Firm* — Alan Kamrath; Kamrath IP Lawfirm, PA

(57) ABSTRACT

A pressure bandage includes a banding portion having opposite first and second sides. A chamber is formed in the first side of the banding portion. The second side of the banding portion includes a hole in communication with the chamber. A bladder is received in the chamber and receives a fluid. The bladder includes an infiltratable surface permeable to the fluid. The infiltratable surface of the bladder and the first side of the banding portion face the same direction. The fluid received in the bladder is permeable out of the bladder via the infiltratable surface. A control member is engaged with the hole of the banding portion and imparts a pressure to the bladder. The hole can be a screw hole, and the control member includes a knob threadedly engaged with the screw hole such that the knob is rotatable to adjust the pressure imparted to the bladder.

6 Claims, 4 Drawing Sheets

PRESSURE BANDAGE

BACKGROUND OF THE INVENTION

1. Field of the Invention

The present invention relates to a pressure bandage and, more particularly, to a pressure bandage allowing a user to adjust a pressure imparted to a treatment part of the user requiring pressurized treatment.

2. Description of the Related Art

Conventional pressurized treatment includes use of a banding portion fixed to a treatment part of a user requiring pressurized treatment. A pump delivers a fluid in a conduit, such that the pressure at the banding portion is greater than atmospheric pressure, maintaining the treatment part in a pressurized status to inhibit growth of the tissue at the treatment part.

In the conventional pressurized treatment, the user can not move freely due to the limitation of the position of the pump for delivering the fluid to the treatment part via the conduit for maintaining the pressure at the treatment part. Thus, the banding portion must be removed when the user intends to move beyond the range of the conduit due to the limitation of the length of the conduit and/or the position of the pump. As a result, the treatment part of the user can not be maintained in the pressurized status, which is inconvenient to use.

Furthermore, the conventional pressurized treatment under positive pressure is a physical therapy achieved by providing a gas or fluid that continuously imparts the positive pressure to the treatment part. However, the treatment effect is limited if the treatment involves an inflammatory, swollen wound or an epithelial tissue requiring ease of pain.

SUMMARY OF THE INVENTION

An objective of the present invention is to provide a pressure bandage allowing a user to adjust the pressure when the difference between the positive pressure in the pressure bandage and atmospheric pressure becomes small, maintaining the pressure bandage in a positive pressure status.

Another objective of the present invention is to provide a pressure bandage using a fluid for medical use via infiltration to immerse or heal the treatment part requiring pressurized treatment.

A further objective of the present invention is to provide a pressure bandage allowing free movement of the user using the pressure bandage.

Still another objective of the present invention is to provide a pressure bandage allowing circulation or replacement of the fluid such that the fluid can be at an appropriate temperature for ease therapy.

The present invention fulfills the above objectives by providing, in a preferred form, a pressure bandage including a banding portion having opposite first and second sides. A chamber is formed in the first side of the banding portion. The second side of the banding portion includes a hole in communication with the chamber. A bladder is received in the chamber and adapted to receive a fluid. The bladder includes an infiltratable surface permeable to the fluid. The infiltratable surface of the bladder and the first side of the banding portion face the same direction. The fluid received in the bladder is permeable out of the bladder via the infiltratable surface. A control member is engaged with the hole of the banding portion and imparts a pressure to the bladder.

In the most preferred form, the hole is a screw hole, and the control member includes a knob threadedly engaged with the screw hole such that the knob is rotatable to adjust the pressure imparted to the bladder.

The present invention will become clearer in light of the following detailed description of illustrative embodiments of this invention described in connection with the drawings.

BRIEF DESCRIPTION OF THE DRAWINGS

The illustrative embodiments may best be described by reference to the accompanying drawings where.

Figure 1:
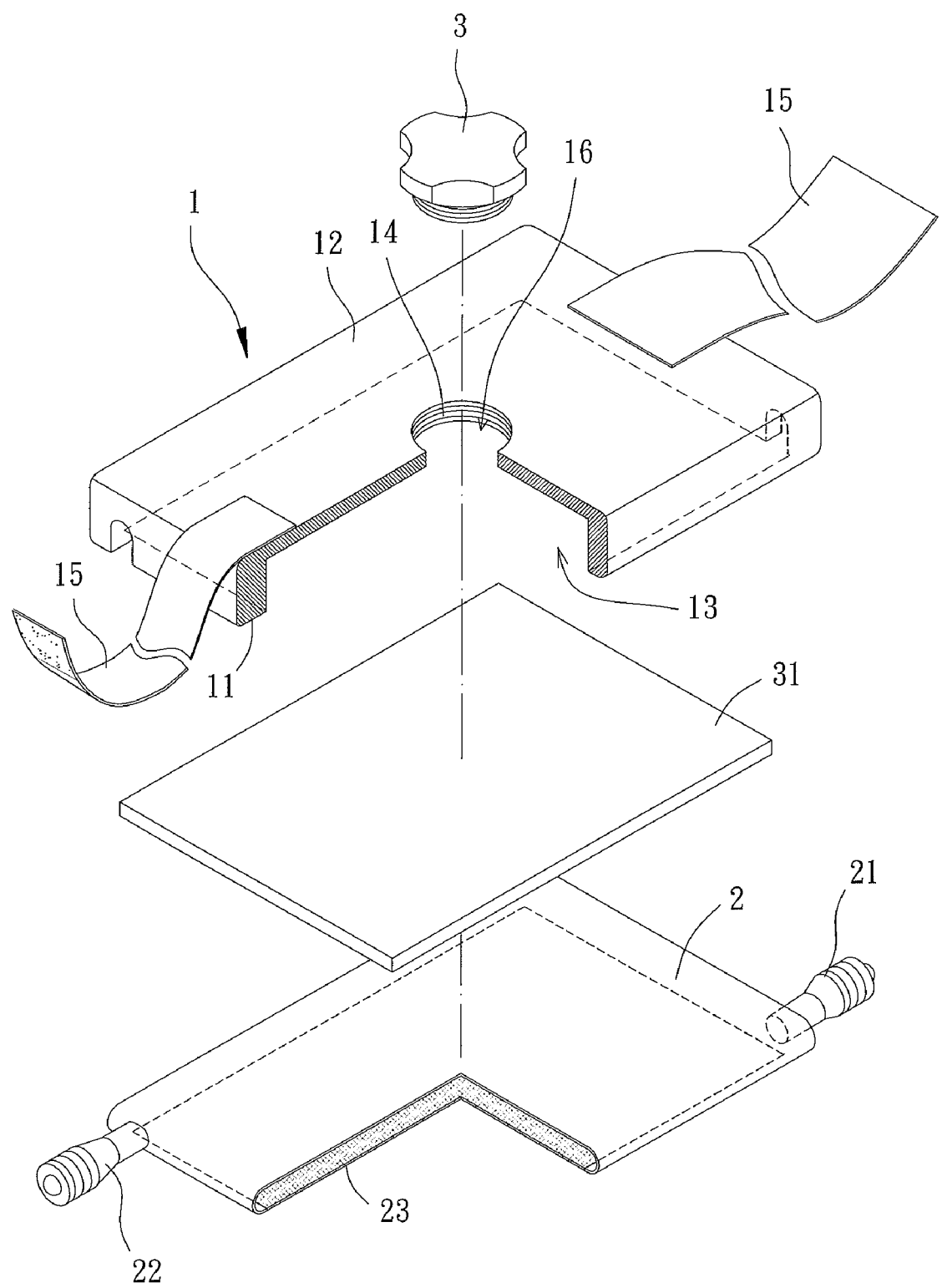
FIG. 1 shows an exploded, perspective view of a pressure bandage according to the preferred teachings of the present invention with portions broken away.
Figure 2:
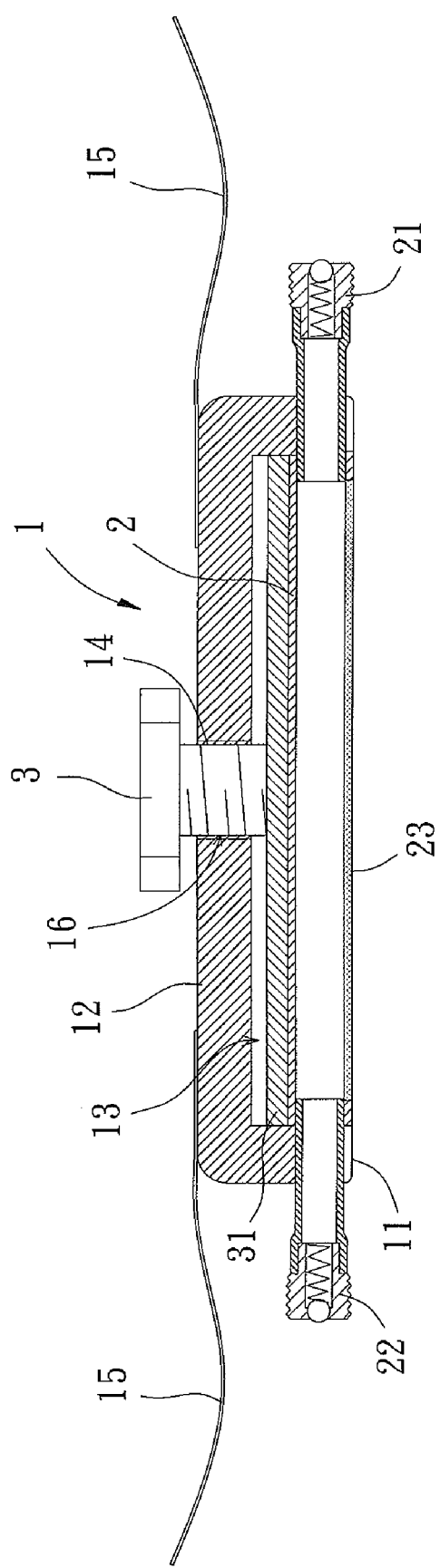
FIG. 2 shows a cross sectional view of the pressure bandage of FIG. 1.

All figures are drawn for ease of explanation of the basic teachings of the present invention only; the extensions of the figures with respect to number, position, relationship, and dimensions of the parts to form the preferred embodiments will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

Where used in the various figures of the drawings, the same numerals designate the same or similar parts. Furthermore, when the terms "first", "second", "side", "portion", "part", "section", and similar terms are used herein, it should be understood that these terms have reference only to the structure shown in the drawings as it would appear to a person viewing the drawings and are utilized only to facilitate describing the invention.

DETAILED DESCRIPTION OF THE INVENTION

A pressure bandage according to the preferred teachings of the present invention is shown in the drawings and generally includes a banding portion 1, a bladder 2 received in the banding portion 1, and a control member 3 for imparting a pressure to the bladder 2.

The banding portion 1 is made of a shapeable sponge, an elastic bandage, or the like. The banding portion 1 can be of any desired shape and size. In the preferred form shown, the banding portion 1 includes opposite first and second sides 11 and 12. A chamber 13 is formed in the first side 11 of the banding portion 1. The second side 12 of the banding portion 1 includes an engaging section 14 having an engaging hole 16 in communication with the chamber 13. In order to easily fix the banding portion 1 to a treatment part 42 of a body portion 44 of a user, the banding portion 1 further includes a fixing member 15. In the most preferred form shown, the fixing member 15 includes two straps respectively having a hook fastener and a loop fastener releasably engaged with the hook fastener, such that the straps can wrap around the body portion 44 of the user and define a space receiving the body portion 44 with the treatment part 42.

The bladder 2 can be fixed in the chamber 13 if desired. The bladder 2 can be comprised of one or more units. In the preferred form shown, the bladder 2 is in the form of a single unit. The bladder 2 is made of deformable material and defines a compartment that can be pressurized to have a pressure greater than atmospheric pressure. Alternatively, a fluid such as a liquid with therapy effect, an anti-inflammatory analgesic, a normal saline, or any liquid having a suitable temperature can be filled into the bladder 2, so that the pressure in the bladder 2 is greater than atmospheric pressure. At least one valve is provided on the bladder 2 to allow filling of the fluid. In the preferred form shown, the bladder 2 includes first and second valves 21 and 22 that are preferably check valves. First and second valves 21 and 22 allow pressurization of the bladder 2 and circulation, supplement, or replacement of the fluid due to a change in the temperature and/or other factors. As an example, the first and second valves 21 and 22 are coupled to external medical treatment equipment, so that the fluid in the bladder 2 can be circulated, removed, or refilled. The bladder 2 includes an infiltratable surface 23 made of semi-permeable membrane. The infiltratable surface 23 of the bladder 2 and the first side 11 of the banding portion 1 face the same direction. The fluid received in the bladder 2 can permeate out of the bladder 2 via the infiltratable surface 23. Thus, the fluid can flow to the treatment part 42 to stimulate the epithelial tissue requiring pressurized treatment to proceed with healing or to provide anti-inflammatory effect.

The control member 3 is engaged with the engaging section 14 and can impart a pressure to the bladder 2 through the hole 16. In the most preferred form shown, the control member 3 includes a knob threadly engaged in the hole 16 in the form of a screw hole. Thus, when the control member 3 is rotated relative to the engaging section 14, the control member 3 presses against and, thus, imparts a pressure to the bladder 2. To impart uniform pressure to the bladder 2, a plate 31 preferably having suitable rigidity is sandwiched between the control member 3 and the bladder 2.

Figure 3:
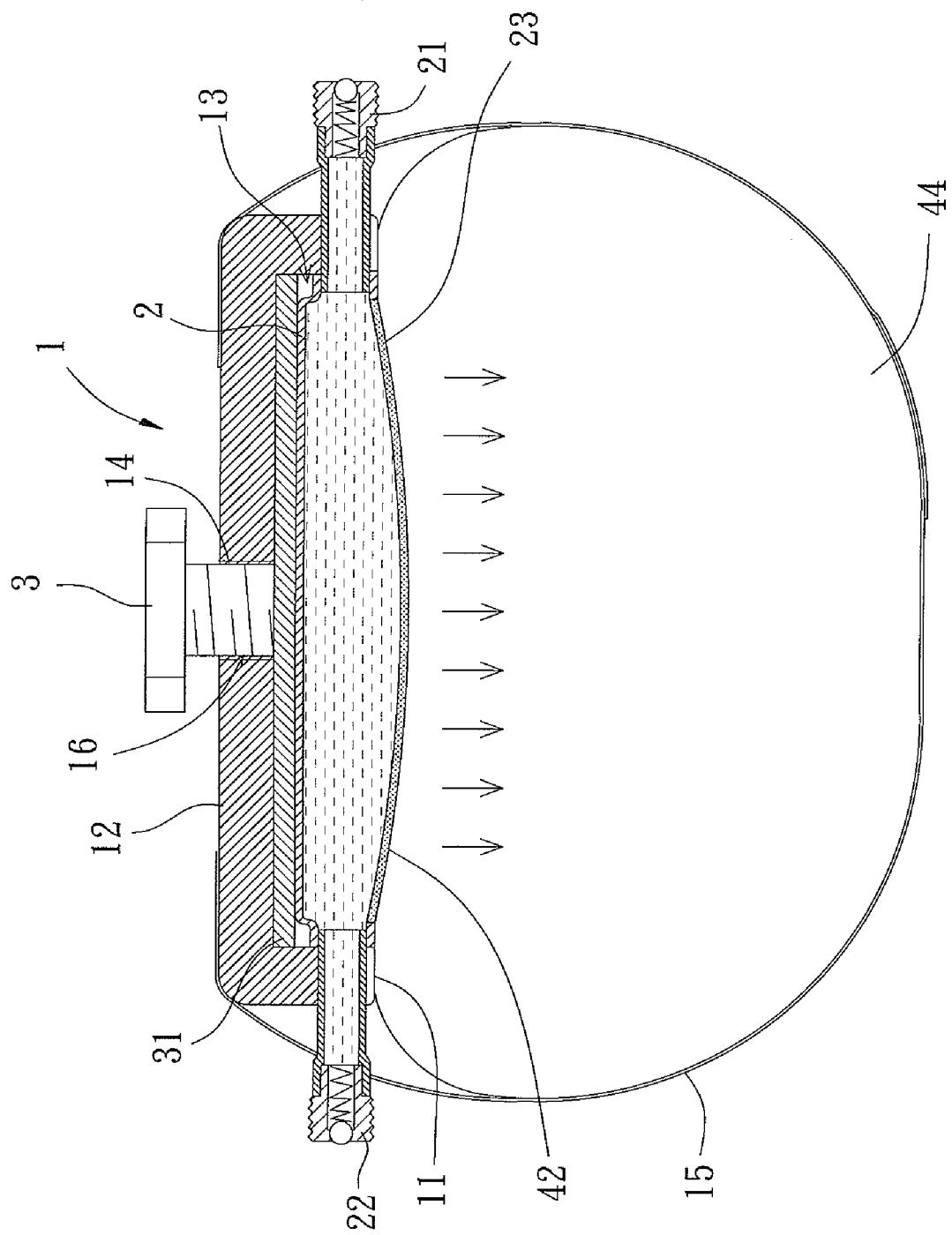
FIG. 3 shows a cross sectional view of the pressure bandage of FIG. 1 mounted to a treatment part.

FIG. 3 shows use of the pressure bandage according to the preferred teachings of the present invention, the infiltratable surface 23 of the bladder 2 is in contact with the treatment part 42 of the user, and the pressure bandage is fixed by the fixing member 15 to the body portion 44 with the treatment part 42. Since the pressure in the bladder 2 is a positive pressure greater than atmospheric pressure, the fluid received in the bladder 2 can permeate out of the bladder 2 to the treatment part 42 while maintaining the treatment part 42 under pressure or maintaining at a suitable temperature for ease therapy effect. The fluid slowly infiltrates the infiltratable surface 23 of the bladder 2 to the treatment part 42 to stimulate the epithelial tissue requiring pressurized treatment to proceed with healing or to provide anti-inflammatory effect.

Figure 4:
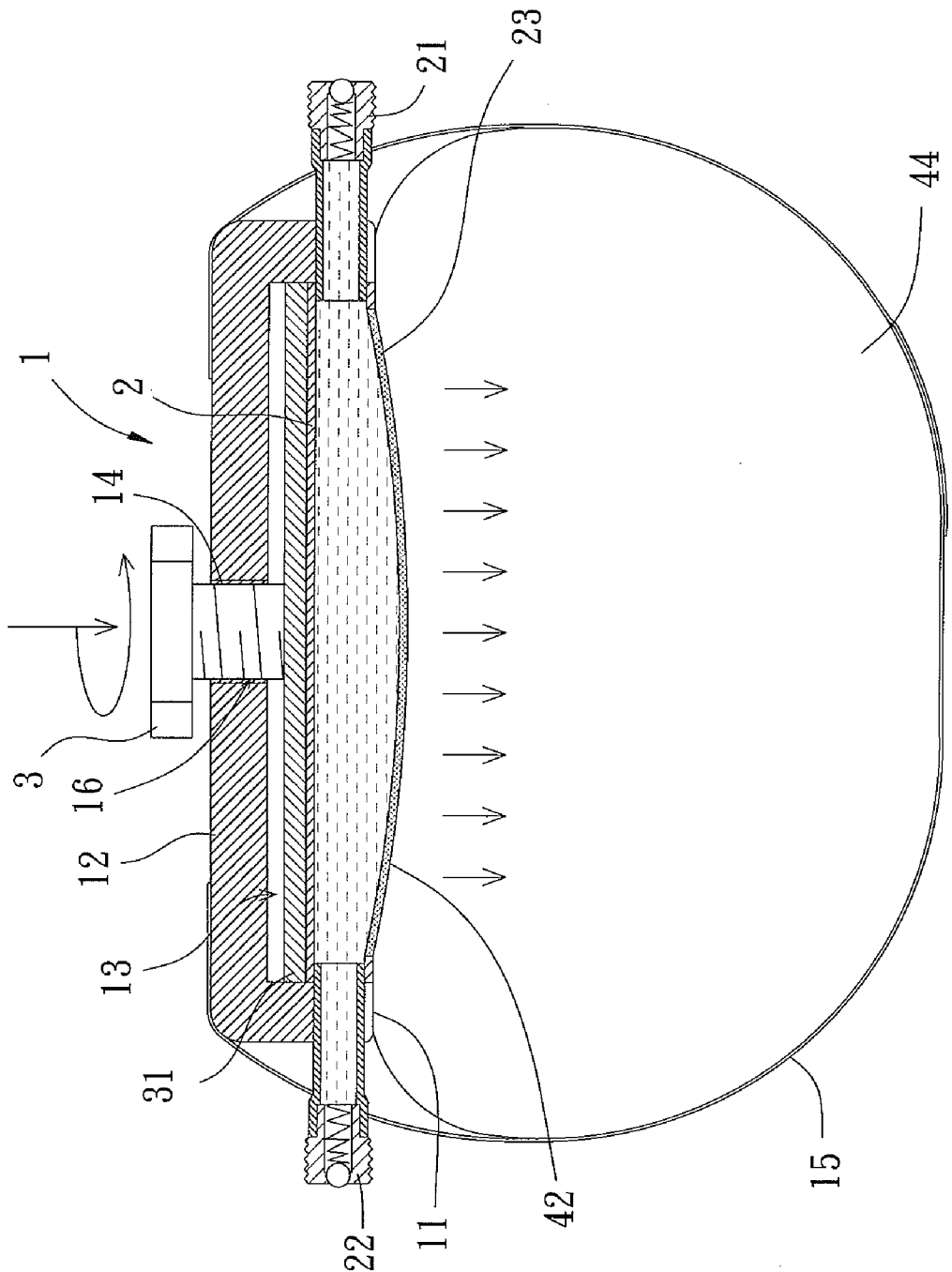
FIG. 4 shows a cross sectional view similar to FIG. 3, illustrating adjustment of pressure imparted to a bladder of the pressure bandage.

With reference to FIG. 4, the greater the amount of the fluid infiltrates out of the bladder 2 via the infiltratable surface 23, the smaller the difference between the pressure in the bladder 2 and atmospheric pressure. When the bladder 2 no longer provides the desired pressurization effect to the treatment part 42, infiltration of the fluid out of the bladder 2 via the infiltratable surface 23 stops. In this case, the user can rotate the control member 3, so that the plate 31 (or the control member 3 itself, if the plate 31 is not utilized) imparts a pressure to the bladder 2, again providing the bladder 2 with a positive pressure greater than atmospheric pressure, as shown in FIG. 4. Thus, the fluid can infiltrate out of the bladder 2 via the infiltratable surface 23 again, providing desired pressure to the treatment part 42. Thus, the pressure bandage according to the preferred teachings of the present invention can easily maintain desired positive pressure at the treatment part 42 requiring pressurized treatment.

When the pressure of the fluid in the bladder 2 can not be increased or when the temperature difference between the fluid and the treatment part 42 is small, suitable measures can be taken to regain the desired pressure or temperature difference. As an example, the fluid in the bladder 2 can be circulated or removed, or fluid can be supplied into the bladder 2 until the fluid in the bladder 2 reaches the desired flow rate, pressure, or temperature.

The pressure bandage according to the preferred teachings of the present invention allows the user to adjust the positive pressure to the treatment part 42 when the pressure difference between the atmospheric pressure and the pressure imparted by the pressure bandage to the treatment part 42 becomes small, allowing continuous use of the pressure bandage under a pressurized status.

The infiltratable surface 23 of the bladder 2 of the pressure bandage according to the preferred teachings of the present invention allows use of fluids for medical treatment via infiltration to immerse or heal the treatment part 42 requiring pressurized treatment.

The pressure bandage according to the preferred teachings of the present invention can be fixed by the fixing member 15 to the treatment part 42, allowing free movement of the user while using the pressure bandage.

The bladder 2 with first and second valves 21 and 22 of the pressure bandage according to the preferred teachings of the present invention allows circulation of the fluid, achieving ease therapy at the treatment part 42 at an appropriate temperature.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:
1. A pressure bandage comprising:
a banding portion including opposite first and second sides, with a chamber formed in the first side of the banding portion, with the second side of the banding portion including a screw hole in communication with the chamber;
a bladder received in the chamber, with the bladder adapted to receive a fluid, with the bladder including an infiltratable surface permeable to the fluid, with the infiltratable surface of the bladder and the first side of the banding portion facing a same direction, with the fluid received in the bladder being permeable out of the bladder via the infiltratable surface; and
a control member including a knob threadedly engaged with the screw hole of the banding portion, with the control member imparting a pressure to the bladder, with the knob rotatable to adjust the pressure imparted to the bladder.

2. The pressure bandage as claimed in claim 1, further comprising: a rigid plate sandwiched between the control member and the bladder, with the control member imparting the pressure to the bladder through the rigid plate.

3. The pressure bandage as claimed in claim 1, with the banding portion including a fixing member, with the fixing member adapted to fix the pressure bandage to a treatment part of a body portion of a user, with the infiltratable surface of the bladder adapted to be in contact with the treatment part, with the fluid being permeable out of the bladder to the treatment part.

4. The pressure bandage as claimed in claim 3, with the fixing member including two straps respectively having a hook fastener and a loop fastener releasably engaged with the hook fastener, with the two straps adapted to wrap around the body portion.

5. The pressure bandage as claimed in claim 1, with the bladder including at least one valve, with said at least one valve adapted for allowing filling of the fluid into the bladder.

6. The pressure bandage as claimed in claim 5, with said at least one valve including two check valves.

\* \* \* \* \*